US008466121B2

(12) United States Patent
Chang et al.

(10) Patent No.: US 8,466,121 B2
(45) Date of Patent: Jun. 18, 2013

(54) METHOD OF SELECTIVELY INHIBITING THE ACTIVITY OF ACAT1 IN THE TREATMENT OF ALZHEIMER'S DISEASE

(75) Inventors: Ta-Yuan Chang, Etna, NH (US); Catherine C. Y. Chang, Etna, NH (US)

(73) Assignee: Trustees of Dartmouth College, Hanover, NH (US)

( * ) Notice: Subject to any disclaimer, the term of this patent is extended or adjusted under 35 U.S.C. 154(b) by 0 days.

(21) Appl. No.: 13/072,915

(22) Filed: Mar. 28, 2011

(65) Prior Publication Data

US 2011/0237656 A1 Sep. 29, 2011

Related U.S. Application Data

(63) Continuation-in-part of application No. PCT/US2009/056601, filed on Sep. 11, 2009.

(60) Provisional application No. 61/103,658, filed on Oct. 8, 2008.

(51) Int. Cl.
*A01N 43/04* (2006.01)
*C12Q 1/68* (2006.01)
*C12N 15/63* (2006.01)
*C07H 21/02* (2006.01)
*C07H 21/04* (2006.01)

(52) U.S. Cl.
USPC ............ 514/44; 435/6; 435/91.1; 435/91.31; 435/455; 536/23.1; 536/24.5

(58) Field of Classification Search
USPC ............. 435/6, 91.1, 91.31, 458, 455; 514/1, 514/2, 44; 536/23.1, 24.5
See application file for complete search history.

(56) References Cited

U.S. PATENT DOCUMENTS

| 2005/0118226 A1 | 6/2005 | Kovacs et al. | 424/423 |
| 2007/0087363 A1 | 4/2007 | Bartel et al. | 435/6 |
| 2008/0177045 A1 | 7/2008 | Lee et al. | 530/388.1 |
| 2009/0004668 A1* | 1/2009 | Chen et al. | 435/6 |

FOREIGN PATENT DOCUMENTS

WO WO 02/44321 * 6/2002

OTHER PUBLICATIONS

Crooke, S., Ann. Rev. Medicine, vol. 55, pp. 61-95 (2004).*
Peracchi et al., Rev. Med. Virol., vol. 14, pp. 47-64 (2004).*
Agrawal et al., Molecular Med. Today., vol. 6, pp. 72-81 (2000).*
Chirila et al., Biomaterials, vol. 23, pp. 321-342 (2002).*
Doench et al, Genes & Development, vol. 17, pp. 438-443 (2003).*
Hollen et al., Nucleic Acids Res., vol. 30, No. 8, pp. 1757-1766 (2002).*
Opalinska et al., Nature Rev., vol. 1, pp. 503-514 (2002).*
Björkhem, I. "Are Side-chain Oxidized Oxysterols Regulators Also in vivo?" Journal of Lipid Research 2009 50:S213-S218.
Chang et al. "Immunological Quantitation and Localization of ACAT-1 and ACAT-2 in Human Liver and Small Intestine" The Journal of Biological Chemistry 2000 275(36):28083-28092.
Giovannoni et al. "Selective ACAT Inhibitors as Promising Antihyperlipidemic, Antiatherosclerotic and Anti-Alzheimer Drugs" Mini Reviews in Medicinal Chemistry 2003 3:576-584.
Halford, R. W. and Russell, D. W. "Reduction of Cholesterol Synthesis in the Mouse Brain Does Not Affect Amyloid Formation in Alzheimer's Disease, but Does Extend Lifespan" Proceedings of the National Academy of Sciences 2009 106(9):3502-3506.
Hudry et al. "Adeno-associated Virus Gene Therapy with Cholesterol 24-Hydroxylase Reduces the Amyloid Pathology Before or After the Onset of Amyloid Plaques in Mouse Models of Alzheimer's Disease" Molecular Therapy 2010 18(1):44-53.
Hutter-Paier et al. "The ACAT Inhibitor CP-113,818 Markedly Reduces Amyloid Pathology in a Mouse Model of Alzheimer's Disease" Neuron 2004 44:227-238.
Huttunen, H. J. and Kovacs, D. M. "ACAT as a Drug Target for Alzheimer's Disease" Neurodegenerative Diseases 2008 5:212-214.
Huttunen et al. "Knockdown of ACAT-1 Reduces Amyloidogenic Processing of APP" Federation of European Biochemical Societies Letters 2007 581(8):1688-1692.
Ikenoya et al. "A Selective ACAT-1 Inhibitor, K-604, Suppresses Fatty Streak Lesions in Fat-fed Hamsters without Affecting Plasma Cholesterol Levels" Atherosclerosis 2007 191:290-297.
Kotti et al. "Brain Cholesterol Turnover Required for Geranylgeraniol Production and Learning in Mice" Proceedings of the National Academy of Sciences 2006 103(10):3869-3874.
Lund et al. "Knockout of the Cholesterol 24-Hydroxylase Gene in Mice Reveals a Brain-specific Mechanism of Cholesterol Turnover" The Journal of Biological Chemistry 2003 278(25):22980-22988.
Scheek et al. "Sphingomyelin Depletion in Cultured Cells Blocks Proteolysis of Sterol Regulatory Element Binding Proteins at Site 1" Proceedings of the National Academy of Sciences 1997 94:11179-11183.
Tabas et al. "Inhibition of Acyl Coenzyme A: Cholesterol Acyl Transferase in J774 Macrophages Enhances Down-regulation of the Low Density Lipoprotein Receptor and 3-Hydroxy-3-methylglutaryl-Coenzyme A Reductase and Prevents Low Density Lipoprotein-induced Cholesterol Accumulation" The Journal of Biological Chemistry 1986 261(7):3147-3155.
International Search Report from PCT/US2009/056607, Feb. 24, 2010.
International Prreliminary Report on Patentability from PCT/US2009/056607, Apr. 21, 2011.

* cited by examiner

*Primary Examiner* — Jane Zara
(74) *Attorney, Agent, or Firm* — Licata & Tyrrell P.C.

(57) ABSTRACT

The present invention features methods for decreasing the size and density of amyloid plaques, decreasing cognitive decline associated with amyloid pathology, and treating Alzheimer's disease by selectively inhibiting the activity of Acyl-CoA:Cholesterol Acyltransferase 1, but not Acyl-CoA: Cholesterol Acyltransferase 2.

6 Claims, No Drawings

METHOD OF SELECTIVELY INHIBITING THE ACTIVITY OF ACAT1 IN THE TREATMENT OF ALZHEIMER'S DISEASE

This application is a continuation-in-part application of PCT/US2009/056601, filed Sep. 11, 2009, which claims the benefit of priority of U.S. Provisional Application No. 61/103,658, filed Oct. 8, 2008, the content of which is incorporated herein by reference in its entirety.

This invention was made with government support under grant number R01HL060306 awarded by the National Institutes of Health. The government has certain rights in the invention.

BACKGROUND OF THE INVENTION

Alzheimer's disease is characterized by two pathological hallmarks, namely extracellular accumulation of plaques, which are aggregates of amyloid beta (Aβ) peptides derived from proteolytic cleavages of amyloid precursor protein (APP), and intracellular accumulation of hyperphosphorylated tau (Hardy & Selkoe (2002) *Science* 297:353-356). APP can be cleaved via two competing pathways, the alpha and the beta secretase pathways, which are distinguished by different subcellular sites of proteolysis and cleavage points within APP (Thinakaran & Koo (2008) *J. Biol. Chem.* 283:29615-29619). Several proteases are capable of producing the alpha-cleavage, after which the gamma-secretase complex that includes presenilin 1 as a catalytic subunit, further cleaves the APP fragment to produce small, non-amyloidogenic fragments. The beta-secretase pathway involves sequential cleavages by beta-secretase and gamma-secretase complexes, and generates Aβ. APP and secretases are all membrane bound proteins/enzymes. Studies have shown that cholesterol content in cells can affect the production of Aβ, in part by the ability of cholesterol to modulate the enzyme activities of various secretases in cell membranes (Wolozin (2004) *Neuron* 41:7-10). Cholesterol metabolism has also been implicated in the pathogenesis of Alzheimer's disease in other manners (Jiang, et al. (2008) *Neuron* 58:681-693; Wellington (2004) *Clin. Genet.* 66:1-16; Hartmann (2001) *Trends Neurosci.* 24:S45-48).

In the brain, cholesterol is derived from endogenous biosynthesis (Dietschy & Turley (2004) *J. Lipid Res.* 45:1375-1397). The transcription factor SREBP2 controls the expression of enzymes involved in cholesterol biosynthesis, including the rate-limiting enzyme HMG-CoA reductase (HMGR) (Goldstein, et al. (2006) *Cell* 124:35-46). Other transcription factors, including liver X receptors (LXRs), control the expression of proteins which function in cholesterol transport (Repa & Mangelsdorf (2000) *Annu. Rev. Cell Dev. Biol.* 16:459-481; Beaven & Tontonoz (2006) *Annu. Rev. Med.* 57:313-329), including apoE, ABCA1, and others (Wang, et al. (2008) *FASEB J.* 22:1073-1082; Tarr & Edwards (2008) *J. Lipid Res.* 49:169-182). In the brain, cholesterol can be enzymatically converted by a brain-specific enzyme, 24-hydroxylase (CYP46A1) (Russell, et al. (2009) *Annu. Rev. Biochem.* 78:1017-1040), to an oxysterol called 24S-hydroxycholesterol (24SOH); the concentration of 24SOH far exceeds those of other oxysterols in the brain (Lutjohann, et al. (1996) *Proc. Natl. Acad. Sci. USA* 93:9799-9804 Bjorkhem (2006) *J. Intern. Med.* 260:493-508; Karu, et al. (2007) *J. Lipid Res.* 48:976-987). Various oxysterols, including 24SOH, can downregulate sterol synthesis in intact cells and in vitro (Song, et al. (2005) *Cell Metab.* 1:179-189; Wang, et al. (2008) *J. Proteome Res.* 7:1606-1614). When provided to neurons, 24SOH decreases the secretion of Aβ (Brown, et al. (2004) *J. Biol. Chem.* 279:34674-34681). However, whether 24SOH or other oxysterols can act in similar fashion(s) in vivo remains to be demonstrated. 24SOH levels have been shown to be decreased in brain samples from Alzheimer's disease patients (Heverin, et al. (2004) *J. Lipid Res.* 45:186-193), suggesting a relationship between 24SOH and Alzheimer's disease.

Acyl-CoA:Cholesterol Acyltransferase (ACAT) converts free cholesterol to cholesterol ester, and is one of the key enzymes in cellular cholesterol metabolism. Two ACAT genes have been identified which encode two different enzymes, ACAT1 and ACAT2 (also known as SOAT1 and SOAT2). While both ACAT1 and ACAT2 are present in the liver and intestine, the cells containing either enzyme within these tissues are distinct, suggesting that ACAT1 and ACAT2 have separate functions. Both enzymes are potential drug targets for treating dyslipidemia and atherosclerosis.

Using the non-selective ACAT inhibitor, CP-113,818 (Chang et al. (2000) *J. Biol. Chem.* 275:28083-28092), Alzheimer's disease-like pathology in the brains of transgenic mice expressing human APP(751) containing the London (V717I) and Swedish (K670M/N671L) mutations has been demonstrated (Hutter-Paier, et al. (2004) *Neuron.* 44(2):227-38). Two months of treatment with CP-113,818 was shown to reduce the accumulation of amyloid plaques by 88%-99% and membrane/insoluble Amyloid β levels by 83%-96%, while also decreasing brain cholesteryl-esters by 86%. Additionally, soluble Amyloid β(42) was reduced by 34% in brain homogenates. Spatial learning was slightly improved and correlated with decreased Amyloid β levels. In nontransgenic littermates, CP-113,818 also reduced ectodomain shedding of endogenous APP in the brain.

A 50% decrease in ACAT1 expression has also been shown to reduce cholesteryl ester levels by 22%, reduce proteolytic processing of APP, and decrease Amyloid β secretion by 40% (Huttunen, et al. (2007) *FEBS Lett.* 581(8):1688-92) in an in vitro neuronal cell line. In this regard, it has been suggested that ACAT inhibition could serve as a strategy to treat Alzheimer's disease (Huttunen & Kovacs (2008) *Neurodegener. Dis.* 5(3-4):212-4).

SUMMARY OF THE INVENTION

The present invention features methods for decreasing the size and density of amyloid plaques, decreasing cognitive decline associated with amyloid pathology, and treating Alzheimer's Disease by administering to a subject in need of treatment an agent that selectively inhibits the expression or activity of Acyl-CoA:Cholesterol Acyltransferase 1 (ACAT1). In one embodiment, the agent has an $IC_H$ value for ACAT1 which is at least twice the corresponding $IC_{50}$ value for ACAT2. In another embodiment, the agent does not inhibit the expression of ACAT1. In an alternative embodiment, the agent is a microRNA molecule. In a further embodiment, the agent has an $IC_{50}$ value in the range of 1 nM to 100 µM. In a particular embodiment of the invention, the agent is selectively delivered to the brain of the subject. In a specific embodiment, the agent is K-604.

DETAILED DESCRIPTION OF THE INVENTION

Amyloid beta-peptide (Abeta or Aβ) accumulation in specific brain regions is a pathological hallmark of Alzheimer's disease (AD). It has now been found that ACAT1, but not ACAT2, plays a significant role in amyloid pathology of AD in vivo. Specifically, ACAT1 modulates the sizes and densities of amyloid plaques and cognitive decline manifested in a mouse model for the AD in vivo. In addition, contrary to previous reports (Hutter-Paier, et al. (2004) supra), it has been shown that ACAT1 deficiency leads to decreases in hAPP, as well as its proteolytic fragments. This finding indicates that ACAT1 deficiency acts to reduce Aβ load mainly by reducing the hAPP protein content. Moreover, ACAT1 deficiency causes an increase in 24SOH content, a decrease in HMGR content, and a decrease in sterol biosynthesis, indicating that 24SOH is a key molecule in regulating brain sterol biosynthesis in vivo. Therefore, ACAT1 has now been definitively shown to be a therapeutic target for treating AD.

Accordingly, the present invention features compositions and methods for decreasing the size and density of amyloid plaques, decreasing cognitive decline associated with amyloid pathology, and treating AD. In accordance with the methods of this invention, a subject having, suspected of having or predisposed to have AD is administered an effective amount of an agent that selectively inhibits the activity of ACAT1 so that the size and density of amyloid plaques in the subject are decreased, cognitive decline associated with amyloid pathology is decreased, and/or the progression of the AD is slowed or prevented thereby treating AD.

As used herein, a "selective inhibitor of ACAT1" or "ACAT1-selective inhibitor" is any molecular species that is an inhibitor of the ACAT1 enzyme but which fails to inhibit, or inhibits to a substantially lesser degree ACAT2. Methods for assessing the selectively of ACAT1 inhibitors are known in the art and can be based upon any conventional assay including, but not limited to the determination of the half maximal (50%) inhibitory concentration (IC) of a substance (i.e., 50% IC, or $IC_{50}$), the binding affinity of the inhibitor (i.e., $K_i$), and/or the half maximal effective concentration ($EC_{50}$) of the inhibitor for ACAT1 as compared to ACAT2. See, e.g., Lada, et al. (2004) *J. Lipid Res.* 45:378-386 and U.S. Pat. No. 5,968,749. ACAT1 and ACAT2 proteins that can be employed in such assays are well-known in the art and set forth, e.g., in GENBANK Accession Nos. NP_000010 (human ACAT1) and NP_005882 (human ACAT2). See also U.S. Pat. No. 5,834,283.

In particular embodiments, a selective inhibitor of ACAT1 is an agent which has an $IC_{50}$ value for ACAT1 that is at least twice or, more desirably, at least three, four, five, or six times higher than the corresponding $IC_{50}$ value for ACAT2. Most desirably, a selective inhibitor of ACAT1 has an $IC_{50}$ value for ACAT1 which is at least one order of magnitude or at least two orders of magnitude higher than the $IC_{50}$ value for ACAT2.

Selective inhibitors of ACAT1 activity have been described. For example, Ikenoya, et al. ((2007) *Atherosclerosis* 191:290-297) teach that K-604 has an $IC_{50}$ value of 0.45 µmol/L for human ACAT1 and 102.85 µmol/L for human ACAT2. As such K-604 is 229-fold more selective for ACAT1 than ACAT2. In addition, diethyl pyrocarbonate has been shown to inhibit ACAT1 with 4-fold greater activity ($IC_{50}$=44 µM) compared to ACAT-2 ($IC_{50}$=170 µM) (Cho, et al. (2003) *Biochem. Biophys. Res. Comm.* 309:864-872). Ohshiro, et al. ((2007) *J. Antibiotics* 60:43-51) teach selective inhibition of beauveriolides I (0.6 µM vs. 20 µM) and III (0.9 µM vs. >20 µM) for ACAT1 over ACAT2. In addition, beauveriolide analogues 258, 280, 274, 285, and 301 show ACAT1-selective inhibition with $pIC_{50}$ values in the range of 6 to 7 (Tomoda & Doi (2008) *Accounts Chem. Res.* 41:32-39). Lada, et al. ((2004) *J. Lipid Res.* 45:378-386) teach a Warner-Lambert compound (designated therein as Compound 1A), and derivatives thereof (designated Compounds 1B, 1C, and 1D), which inhibit ACAT1 more efficiently than ACAT2 with $IC_{50}$ values 66- to 187-fold lower for ACAT1 than for ACAT2. Moreover, Lee, et al. ((2004) *Bioorg. Med. Chem. Lett.* 14:3109-3112) teach methanol extracts of *Saururus chinensis* root that contain saucerneol B and manassantin B for inhibiting ACAT activity. Saucerneol B inhibited hACAT-1 and hACAT-2 with $IC_{50}$ values of 43.0 and 124.0 µM, respectively, whereas manassantin B inhibited hACAT-1 and hACAT-2 with $IC_{50}$ values of 82.0 µM and only 32% inhibition at 1 mM, respectively.

Desirably, ACAT1-selective inhibitors of the present invention have an $IC_{50}$ value in the range of 1 nM to 100 µM. More desirably, ACAT1-selective inhibitors of the invention have an $IC_{50}$ value less than 100 µM, 50 µM, 10 µM, or 1 µM. Most desirably, ACAT1-selective inhibitors of the invention have an $IC_{50}$ value in the nM range (e.g., 1 to 999 nM).

In addition to the above-referenced ACAT1-selective inhibitors, it is contemplated that any conventional drug screening assay can be employed for identifying or selecting additional or more selective ACAT1 inhibitors or derivatives or analogs of known ACAT1 inhibitors. See, e.g., Lada, et al. (2004) *J. Lipid Res.* 45:378-386. Such agents can be identified and obtained from libraries of compounds containing pure agents or collections of agent mixtures. Examples of pure agents include, but are not limited to, proteins, peptides, nucleic acids, oligonucleotides, carbohydrates, lipids, synthetic or semi-synthetic chemicals, and purified natural products. Examples of agent mixtures include, but are not limited to, extracts of prokaryotic or eukaryotic cells and tissues, as well as fermentation broths and cell or tissue culture supernates. In the case of agent mixtures, one may not only identify those crude mixtures that possess the desired activity, but also monitor purification of the active component from the mixture for characterization and development as a therapeutic drug. In particular, the mixture so identified may be sequentially fractionated by methods commonly known to those skilled in the art which may include, but are not limited to, precipitation, centrifugation, filtration, ultrafiltration, selective digestion, extraction, chromatography, electrophoresis or complex formation. Each resulting subtraction may be assayed for the desired activity using the original assay until a pure, biologically active agent is obtained.

Library screening can be performed in any format that allows rapid preparation and processing of multiple reactions such as in, for example, multi-well plates of the 96-well variety. Stock solutions of the agents as well as assay components are prepared manually and all subsequent pipetting, diluting, mixing, washing, incubating, sample readout and data collecting is done using commercially available robotic pipetting equipment, automated work stations, and analytical instruments for detecting the signal generated by the assay. Examples of such detectors include, but are not limited to, luminometers, spectrophotomers, calorimeters, and fluorimeters, and devices that measure the decay of radioisotopes. It is contemplated that any suitable ACAT enzymatic assay can be used in such screening assays. Moreover, preclinical efficacy of ACAT1 inhibitors can be assessed using, conventional animal models of AD.

As disclosed herein, there are a number of suitable molecules that selectively inhibit the activity of ACAT1 without modulating the expression of ACAT1. Accordingly, in one embodiment of the present invention, a "selective inhibitor of ACAT1" specifically excludes molecules siRNA, antisense molecules, or ribozymes. However, in alternative embodiments, the ACAT1 selective inhibitor is a molecule, which selectively inhibits the expression of ACAT1, without modulating the expression of ACAT2. In so far as some RNAi molecules have been shown to induce significant neurotoxicity in brain tissue (McBride, et al. (2008) *Proc. Natl. Acad.*

*Sci. USA* 105:5868-5873), specific embodiments of this invention embrace one or more microRNA molecules as the ACAT1-selective inhibitor. As is conventional in the art, miRNA or microRNA refer to 19-25 nucleotide non-coding RNAs derived from endogenous genes that act as post-transcriptional regulators of gene expression. They are processed from longer (ca 70-80 nucleotide) hairpin-like precursors termed pre-miRNAs by the RNAse III enzyme Dicer. MicroRNAs assemble in ribonucleoprotein complexes termed miRNPs and recognize their target sites by antisense complementarity thereby mediating down-regulation of their target genes. By way of illustration, target sequences for mouse ACAT1 microRNA molecules include, but are not limited to, those listed in Table 2 as SEQ ID NOs:37-40. Artificial microRNAs against human ACAT1 gene (e.g., GENBANK Accession No. NM_000019, incorporated by reference) were also generated and shown to decrease human ACAT1 protein expression by 80% in human cells. Exemplary microRNA sequences targeting human ACAT1 include, but are not limited, those listed in Table 4. In a similar manner, microRNA against the ACAT1 gene in primates (e.g., GENBANK Accession No. XM_508738, incorporated by reference) can be developed, and used to selectively inhibit the expression of primate ACAT1.

MicroRNA molecules which selectively inhibit the expression of ACAT1 can be administered as naked molecules or via vectors (e.g., a plasmid or viral vector such as an adenoviral, lentiviral, retroviral, adeno-associated viral vector or the like) harboring nucleic acids encoding the microRNA. Desirably, a vector used in accordance with the invention provides all the necessary control sequences to facilitate expression of the microRNA. Such expression control sequences can include but are not limited to promoter sequences, enhancer sequences, etc. Such expression control sequences, vectors and the like are well-known and routinely employed by those skilled in the art.

As indicated, selective inhibitors of ACAT1 find application in methods for decreasing the size and density of amyloid plaques, decreasing cognitive decline associated with amyloid pathology, and treating AD. Generally, such methods involve administering to a subject in need of treatment a selective inhibitor of ACAT1 in an amount that effectively reduces the activity of ACAT1 by at least 60%, 70%, 80%, 90%, 95%, 99% or 100%. Subjects benefiting from treatment with an agent of the invention include subjects confirmed as having AD, subjects suspected of having AD, or subjects at predisposed to have AD (e.g., subjects with a family history or Down syndrome for Alzheimer's disease). In the context of this invention, a subject can be any mammal including human, companion animals (e.g., dogs or cats), livestock (e.g., cows, sheep, pigs, or horses), or zoological animals (e.g., monkeys). In particular embodiments, the subject is a human.

While certain embodiments of this invention embrace in vivo applications, in vitro use of agents of the invention are also contemplated for examining the effects of ACAT1 inhibition on particular cells, tissues or regions of the brain. In addition to treatment, agents of the invention also find application in monitoring the phenotypic consequences (e.g., rate of plaque formation or rate of cognitive decline) of amyloid pathology in rodent models of AD.

When used in therapeutic applications, an ACAT1-selective inhibitor of the invention will have the therapeutic benefit of decreasing the size and density of amyloid plaques in the subject, decreasing or slowing the cognitive decline associated with amyloid pathology in the subject, and/or treating AD in the subject as compared to subjects not receiving treatment with the ACAT1-selective inhibitor. An ACAT1-selective inhibitor of the invention is expected to decrease the size and density of amyloid plaques in a subject by 10%, 20%, 30%, 40%, 50%, 60% or more as compared to an untreated subject. Similarly, an ACAT1-selective inhibitor of the invention is expected to decrease or slow the cognitive decline associated by amyloid pathology by 10%, 20%, 30%, 40%, 50%, 60% or more as compared to an untreated subject (e.g., as determined by Blessed Information-Memory-Concentration Test, the Blessed Orientation-Memory-Concentration Test, and the Short Test of Mental Status, or the Mini-Mental State Examination). Cognitive assessment can include monitoring of learning and retaining new information (e.g., does the subject have trouble remembering recent conversations, events, appointments; or frequently misplace objects), monitoring handling of complex tasks (e.g., can the subject follow a complex train of thought, perform tasks that require many steps such as balancing a checkbook or cooking a meal), monitoring reasoning ability (e.g., is the subject able to respond with a reasonable plan to problems at work or home, such as knowing what to do if the bathroom flooded), monitoring subject's spatial ability and orientation (e.g., can the subject drive, organize objects around the house, or find his or her way around familiar places), and/or monitoring language (e.g., does the subject have difficulty finding words to express what he or she wants to say and with following conversations). Based upon a decrease in signs and symptoms of AD, it is expected that AD in a subject receiving treatment will be prevented or slowed thereby treating the AD.

Successful clinical use of an ACAT1-selective inhibitor can be determined by the skilled clinician or veterinarian based upon routine clinical practice, e.g., by monitoring cognitive decline via methods disclose herein, functional activities (e.g., the Functional Activities Questionnaire), and sensory impairment and physical disability according to methods known in the art.

For therapeutic use, ACAT1-selective inhibitors can be formulated with a pharmaceutically acceptable carrier at an appropriate dose. Such pharmaceutical compositions can be prepared by methods and contain carriers which are well-known in the art. A generally recognized compendium of such methods and ingredients is Remington: The Science and Practice of Pharmacy, Alfonso R. Gennaro, editor, 20th ed. Lippincott Williams & Wilkins: Philadelphia, Pa., 2000. A pharmaceutically acceptable carrier, composition or vehicle, such as a liquid or solid filler, diluent, excipient, or solvent encapsulating material, is involved in carrying or transporting the subject agent from one organ, or portion of the body, to another organ, or portion of the body. Each carrier must be acceptable in the sense of being compatible with the other ingredients of the formulation and not injurious to the patient.

Examples of materials which can serve as pharmaceutically acceptable carriers include sugars, such as lactose, glucose and sucrose; starches, such as corn starch and potato starch; cellulose, and its derivatives, such as sodium carboxymethyl cellulose, ethyl cellulose and cellulose acetate; powdered tragacanth; malt; gelatin; talc; excipients, such as cocoa butter and suppository waxes; oils, such as peanut oil, cottonseed oil, safflower oil, sesame oil, olive oil, corn oil and soybean oil; glycols, such as propylene glycol; polyols, such as glycerin, sorbitol, mannitol and polyethylene glycol; esters, such as ethyl oleate and ethyl laurate; agar; buffering agents, such as magnesium hydroxide and aluminum hydroxide; alginic acid; pyrogen-free water; isotonic saline; Ringer's solution; ethyl alcohol; pH buffered solutions; polyesters, polycarbonates and/or polyanhydrides; and other non-toxic compatible substances employed in pharmaceutical formulations. Wetting agents, emulsifiers and lubricants, such as sodium lauryl sulfate and magnesium stearate, as well as coloring agents, release agents, coating agents, sweetening, flavoring and perfuming agents, preservatives and antioxidants can also be present in the compositions.

Compositions of the present invention can be administered parenterally (for example, by intravenous, intraperitoneal, subcutaneous or intramuscular injection), topically, orally, intranasally, intravaginally, or rectally according to standard medical practices.

In certain embodiments of the present invention, the ACAT1-selective inhibitor is selectively delivered to the brain. For the purposes of the present invention, "selective delivery to the brain" or "selectively delivered to the brain" is intended to mean that the agent is administered directly to the brain of the subject (e.g., by a shunt or catheter; see, e.g., U.S. Patent Application No. 20080051691), to the perispinal space of the subject without direct intrathecal injection (see, e.g., U.S. Pat. No. 7,214,658), or in a form which facilitates delivery across the blood brain barrier thereby reducing potential side effects associated with ACAT1 inhibition in other organs or tissues. In this regard, formulation of the agent into a nanoparticle made by polymerization of a monomer (e.g., a methylmethacrylate, polylactic acid, polylactic acid-polyglycolic acid-copolymer, or polyglutaraldehyde) in the presence of a stabilizer allows passage of the blood brain barrier without affecting other organs with the agent. See, e.g., U.S. Pat. No. 7,402,573, incorporated herein by reference in its entirety. Moreover, an exemplary system for selectively delivering microRNAs to the brain is the Adeno-Associated Virus (AAV) vector system. See, e.g., Cearley & Wolfe (2007) *J. Neurosc.* 27(37):9928-9940.

The selected dosage level of an ACAT1-selective inhibitor will depend upon a variety of factors including the activity of the particular agent of the present invention employed, the route of administration, the time of administration, the rate of excretion or metabolism of the particular agent being employed, the duration of the treatment, other drugs, compounds and/or materials used in combination with the particular agent employed, the age, sex, weight, condition, general health and prior medical history of the patient being treated, and other factors well-known in the medical arts.

A physician or veterinarian having ordinary skill in the art can readily determine and prescribe the effective amount of the pharmaceutical composition required based upon the administration of similar compounds or experimental determination. For example, the physician or veterinarian could start doses of an agent at levels lower than that required in order to achieve the desired therapeutic effect and gradually increase the dosage until the desired effect is achieved. This is considered to be within the skill of the artisan and one can review the existing literature on a specific agent or similar agents to determine optimal dosing.

The invention is described in greater detail by the following non-limiting examples.

Example 1

Methods

Mice.

Mice were fed ad libitum with standard chow diet, maintained in a pathogen-free environment in single-ventilated cages and kept on a 12 hour light/dark schedule.

Generation of Acat1−/−Alz (A1−/Alz) and Acat2−/−/Alz (A2−/Alz) Mice.

Acat1−/− and Acat2−/− mice (Meiner, et al. (1996) *Proc. Natl. Acad. Sci. USA* 93:14041-14; Buhman, et al. (2000) *Nat. Med.* 6:1341-1347) in C57BL/6 background are known in the art. The 3XTg-Alz mice (Alzheimer's disease mice) in hybrid 129/C57BL/6 background contain two mutant human transgenes, hAPP harboring Swedish mutation (hAPPswe), and mutant htau (htau$_{P301L}$) under a neuron-specific promoter, and contain the knock-in mutant presenilin 1 (PS1$_{M146V}$) (Oddo, et al. (2003) *Neuron* 39:409-421).

Mouse Tissue Isolation.

Animals were sacrificed by $CO_2$ asphyxiation. The brains, adrenals and livers were rapidly isolated. Mice brains were dissected into various regions on ice within 5 minutes and were either used fresh (for ACAT enzyme activity assay) or were rapidly frozen on dry ice for other usage.

ACAT Activity Assay, Immunoprecipitation (IP) and Immunoblot Analyses.

Freshly isolated tissue samples were homogenized on ice in 50 mM Tris, 1 mM EDTA, pH 7.8 and solubilized in detergent using 2.5% CHAPS and 1 M KCl. The homogenates were centrifuged at 100,000 g for 45 minutes. The supernatants were used for ACAT activity assay in mixed micelles, and for IP and immunoblot analyses (Chang, et al. (1998) *J. Biol. Chem.* 273:35132-35141; Chang, et al. (2000) *J. Biol. Chem.* 275:28083-28092).

RNA Isolation, RT-PCR, and Real-Time PCR.

Total RNA was isolated with TRIZOL reagent (Invitrogen), stored at −80° C., and used for RT-PCR experiments, using the protocol supplied by the manufacturer. Real-time PCR was performed using the DYNAMO HS SYBR Green qPCR kit (New England Biolabs). Relative quantification was determined by using the delta delta CT method (Pfaffl, et al. (2002) *Nucleic Acids Res.* 30:e36). Mouse ACAT1 and human APP primers were designed using Oligo 4.0 Primer Analysis Software. Mouse ACAT2, neurofilament 120-kD (NF120), GAPDH primers sequences are known in the art (Sakashita, et al. (2003) *Lab. Invest.* 83:1569-1581; Kuwahara, et al. (2000) *Biochem. Biophys. Res. Commun.* 268:763-766; Pan, et al. (2007) *BMC Mol. Biol.* 8:22). Sequences of primers used herein are listed in Table 1.

TABLE 1

| Gene | Amplicon Size | Sense/Antisense (5'->3') | SEQ ID NO: |
|---|---|---|---|
| ACAT1 | 274 | AGCCCAGAAAAATTTCATGGACACATACAG | 1 |
|  |  | CCCTTGTTCTGGAGGTGCTCTCAGATCTTT | 2 |
| ACAT2 | 530 | TTTGCTCTATGCCTGCTTCA | 3 |
|  |  | CCATGAAGAGAAAGGTCCACA | 4 |
| GAPDH | 186 | ATGGTGAAGGTCGGTGTG | 5 |
|  |  | CATTCTCGGCCTTGACTG | 6 |
| NF120 | 382 | ACGGCGCTGAAGGAGATC | 7 |
|  |  | GTCCAGGGCCATCTTGAC | 8 |
| HUMAN APP | 260 | CCCACTGATGGTAATGCTGGC | 9 |
|  |  | GGAATCACAAAGTGGGGATGG | 10 |
| ABCA1 | 96 | GGTTTGGAGATGGTTATACAATAGTTGT | 11 |
|  |  | TTCCCGGAAACGCAAGTC | 12 |
| ABCG1 | 85 | AGGTCTCAGCCTTCTAAAGTTCCTC | 13 |
|  |  | TCTCTCGAAGTGAATGAAATTTATCG | 14 |
| ABCG4 | 541 | CTGTCCTATTCCGTGCGGGA | 15 |
|  |  | GGGACTTCATGAGGGACACCACTT | 16 |

TABLE 1-continued

| Gene | Amplicon Size | Sense/Antisense (5'->3') | SEQ ID NO: |
|---|---|---|---|
| APOE | 130 | AGCCAATAGTGGAAGACATGCA | 17 |
| | | GCAGGACAGGAGAAGGATACTCAT | 18 |
| CYP46A1 | 266 | CAGTGAAGGTCATGCTGGAG | 19 |
| | | CGCAATGAAGAAGGTGACAA | 20 |
| HMGR | 69 | TCTGGCAGTCAGTGGGAACTATT | 21 |
| | | CCTCGTCCTTCGATCCAATTT | 22 |
| HMGS | 77 | GCCGTCAACTGGGTCGAA | 23 |
| | | GCATATATAGCAATGTCTCCTGCA | 24 |
| HPRT | 91 | TTGCTCGAGATGTCATGAAGGA | 25 |
| | | AGCAGGTCAGCAAAGAACTTATAGC | 26 |
| LDLR | 68 | CTGTGGGCTCCATAGGCTATCT | 27 |
| | | GCGGTCCAGGGTCATCTTC | 28 |
| LRP | 95 | TGGGTCTCCCGAAATCTGTT | 29 |
| | | ACCACCGCATTCTTGAAGGA | 30 |
| SREBP1 | 121 | AACCAGAAGCTCAAGCAGGA | 31 |
| | | TCATGCCCTCCATAGACACA | 32 |
| SREBP2 | 150 | GTGGAGCAGTCTCAACGTCA | 33 |
| | | TGGTAGGTCTCACCCAGGAG | 34 |
| SQS | 137 | CCAACTCAATGGGTCTGTTCCT | 35 |
| | | TGGCTTAGCAAAGTCTTCCAACT | 36 |

The PCR reaction conditions for amplification of ACAT1, ACAT2, GAPDH, NF120 and Human APP included an initial denaturation at 94° C. for 5 minutes. Subsequently, 40 cycles of amplification were performed which included: denaturation at 94° C. for 10 seconds, annealing at 56° C. for 20 seconds, and elongation at 72° C. for 29 seconds. Amplification conditions for the remaining primers listed in Table 1 were as previously described (Van Eck, et al. (2003) *J. Biol. Chem.* 278:23699-23705).

In Situ Hybridization, Immunohistochemical and Thioflavin S Staining.

In situ hybridization was performed using standard procedures (Poirier, et al. (2008) *J. Biol. Chem.* 283:2363-2372) Immunohistochemistry was performed according to standard methods (Oddo, et al. (2003) supra). Thioflavin S staining was according to the protocol as described (Guntern, et al. (1992) *Experientia* 48:8-10), using free-floating sections. Confocal analysis of thioflavin S-positive amyloid deposits was performed using known methods (Dickson & Vickers (2001) *Neuroscience* 105:99-107).

Preparation of Brain Homogenates and Immunoblot Analysis of APP and Its Fragments, and Human Tau.

Brain homogenates were prepared in the sucrose buffer with protease inhibitors at 4° C. according to published protocol (Schmidt, et al. (2005) *Methods Mol. Biol.* 299:267-278). Aliquots of homogenates were quickly frozen on dry ice and stored at −80° C. Upon usage, frozen homogenates were thawed on ice and centrifuged for 1 hour at 100,000 g at 4° C.; the supernatants contained soluble proteins including sAPPα and sAPPβ, while the pellet contained membrane-associated, insoluble proteins including full-length APP, CTFα, CTFβ, etc. Immunoblot analysis of APP and its fragments was according to (Cheng, et al. (2007) *J. Biol. Chem.* 282:23818-23828). The following antibodies were used: anti-human-Aβ 6E10 (1:5000) (Covance), anti-human-APP 369 antiserum (1:1000), anti-human-tau HT7 (1:1000) (Pierce), anti-human-tau phosphorylated at Ser202 AT8 (1:1000) (Peirce), monoclonal anti-HMG-CoA reductase IgG-A9 (1:3) (obtained from ATCC), and β-actin (1:5000) (Sigma). Densitometric analysis was performed using NIH Image software.

Aβ Analysis by ELISA.

Samples were prepared according to a standard protocol (Schmidt, et al. (2005) *Methods Mol. Biol.* 299:279-297), loaded undiluted or diluted 5-10 fold onto the "human β amyloid (1-40)" or "human β Amyloid (1-42)" ELISA plate (Wako), and analyzed according to protocol provided by Wako.

Contextual Fear Conditioning.

Contextual fear conditioning was performed according to a published protocol (Comery, et al. (2005) *J. Neurosci.* 25:8898-8902; Jacobsen, et al. (2006) *Proc. Natl. Acad. Sci. USA* 103:5161-5166). The auditory cue was from e2s (London, U.K.). GoldWave software program was used to edit the auditory cue; Winamp software was used to play the cue sound using the speakers. The digital sound level meter (RadioShack) was used to adjust the cue sound level to 87 dB. Each mouse behavior was recorded using a computer webcam (QuickCam from Logitech) and ANY-maze recording software. The videos were analyzed for freezing behavior, using time sampling at 5 second intervals.

Sterol Composition Analysis in Mice Brains.

Mice forebrains were homogenized and extracted using chloroform:methanol (2:1) (at 12 ml final vol. per mouse brain), dried down under nitrogen, and redissolved in MeOH. Ten percent of the sample was placed in a 2 ml GC/MS autosampler vial, dried down, and trimethyl-silyl derivatized overnight at room temperature with 0.5 ml TRI-SIL TBT (Pierce). One microliter of derivatized sample (or 0.1 µl for cholesterol measurements) was injected into a Shimadzu QP 2010 GC-Mass instrument. GC/MS analysis of sterols was according to known methods (Ebner, et al. (2006) *Endocrinology* 147:179-190) with modifications, using selected ion monitoring (cholesterol: 24 329, 353, 368, 458; desmosterol: 441, lanosterol: 393; 24S-hydroxycholesterol: 413) and standard curves for quantification.

Sterol, Fatty Acid and Cholesterol Ester Synthesis in Mice Brains.

Sterol and fatty acid synthesis in mice brains was measured according to known methods (Reid, et al. (2008) *J. Neurosci. Methods* 168:15-25). A similar method was developed to measure cholesterol esterification from $^3$H-cholesterol in vivo: mice were anesthetized with ketamine xylazine (0.1 ml/30 g body weight), mounted onto the Kopf stereotaxic instrument. After sagittal skin incision, $^3$H cholesterol at 10 µCi/mouse prepared in 3 µl of 5 mM methyl beta-cylodextrin in PBS was injected into the right lateral ventricle with a glass syringe in 2 minutes. Mice were kept in cages for 3 hours, then euthanized by $CO_2$ gas. The forebrains were removed; lipids were extracted and redissolved in MeOH as described earlier. Ten percent of the redissolved sample was analyzed by TLC, using plates from Analtech, using solvent system hexanes:ethyl ether (anhydrous): acetic acid (60:40:1). The cholesterol and $^3$H cholesterol ester (CE) bands were scraped off the TLC plate and counted. Percent cholesterol esterification was determined by dividing the CE count by the total $^3$H cholesterol count.

Sterol Synthesis and Cholesterol Esterification in Primary Neuronal Cell Culture.

Hippocampal neurons were isolated from A1+/Alz and A1−/Alz mice at postnatal day 5 according to standard protocols (Brewer (1997) *J. Neurosci. Methods* 71:143-155; Price & Brewer (2001) *In Protocols for Neural Cell Culture.* Fedoroff & Richardson, editors. Totowa, N.J.: Humana Press, Inc. 255-264). Cells were seeded in 6-well dishes in triplicates at 300,000 cells/well, and grown in 3 ml/well Neurobasal A medium with 1×B27, 0.5 mM L-Gln and 5 ng/ml FGF for 14 days. Half of the medium was replaced with fresh media once every 7 days. Forty-eight hours after the second media replacement, 50 µCi of [$^3$H] sodium acetate (100 mCi/mmol) in PBS was added per well for 3 hours. Lipids in cells and in media were extracted, saponified, and analyzed by using the same TLC system described herein. To minimize sterol oxidation, samples were protected from light and heat during lipid extraction, and were analyzed without storage. To improve separation, after sample loading, the TLC plate was placed under vacuum for 30 minutes prior to chromatography. $^3$H-labeled sterol bands were identified based on iodine staining of unlabeled sterols added to samples prior to lipid extraction. Rf values: lanosterol, 0.5; cholesterol, 0.38; 24SOH, 0.2. The bands were scraped off and counted. For each labeled sterol, the counts present in cells and in media were added to calculate the synthesis rate for that sterol. Cholesterol esterification in intact cells was conducted according to established methods (Chang, et al. (1986) *Biochemistry* 25:1693-1699); the $^3$H-oleate pulse time was 3 hours.

Statistical Analysis.

Statistical comparisons were made by using a two-tailed, unpaired Student's-test. The difference between two sets of values was considered significant when the P value was less than 0.05. Symbols used: *p<0.05; p<0.01; *p<0.001.

Example 2

ACAT Expression in Mouse Brains

Whether the brain has ACAT enzyme activity has not been previously shown. Therefore, to examine this, brain homogenates were prepared from wild-type, Acat1−/− (A1−) and Acat2−/− (A2−) mice. This analysis indicated that wild-type and A2− mouse brains contained comparable ACAT enzyme activity, while A1− mice brains contained negligible activity. Various brain regions prepared from wild-type mice all contained ACAT activities, while those from A1− mice brain contained no activity. Mouse ACAT1 is a 46-kDa protein (Meiner, et al. (1997) *J. Lipid Res.* 38:1928-1933). Immunoblot analysis showed that in homogenates prepared from mouse brain (but not from other mouse tissues), a non-ACAT1 protein band appeared in the 46-kDa region; the presence of this non-specific band precluded the use of immunoblotting or histochemical staining to identify ACAT1 in the mouse brain. To unambiguously identify ACAT1 protein, immunoprecipitation (IP) experiments were performed using detergent solubilized wild-type mouse brain extracts. The results of the IP experiment showed that ACAT activity could be efficiently immunodepleted by ACAT1-specific antibodies, but not by control antibodies. Immunoblot analysis of the immunoprecipates was then performed. The results showed that in homogenates from wild-type mouse brain regions, the ACAT1 antibodies specifically identified a 46-kDa-protein band; control experiments showed that this band was absent in homogenates prepared from the adrenals and brains of A1− mice. This result indicated that mouse brains express ACAT1 as the major ACAT isoenzyme.

To determine the ACAT1 mRNA distribution in mouse brains, in situ hybridization experiments were performed. Both hippocampus and cortex contain ACAT1 mRNA; with hippocampus showing a stronger signal. Other ACAT1 positive regions included choroids plexus, medial habenular nucleus, amygdala, and rostral extension of the olfactory peduncle. Subsequently, hippocampus-rich regions and cortex-rich regions were isolated from wild-type mice and their ACAT1 mRNA levels were compared by real-time PCR. The result validated the in situ hybridization experiment, and showed that ACAT1 mRNA was ~2-fold higher in hippocampus than in cortex. A separate, RT-PCR experiment using ACAT2-specific primers showed that only the thalamus-rich region, but no other brain regions, expressed low but detectable ACAT2 mRNA. It has similarly been shown that monkey brains have nearly undetectable levels of ACAT2 mRNA (Anderson, et al. (1998) *J. Biol. Chem.* 273:26747-26754).

Example 3

ACAT1-Deficient Alzheimer's Mice

While non-selective ACAT inhibition has suggested a role for ACAT activity in Alzheimer's pathology, it had not been shown whether the effects of the ACAT inhibitor acted by inhibiting ACAT activity and/or other biological process(es) in the mice brains. Accordingly, a genetic approach was employed to definitively assess the role of each isoenyzme in the pathology of Alzheimer's Disease. To carry out this analysis, a triple transgenic Alzheimer's mouse model (3XTg-Alz; Oddo, et al. (2003) supra), which has been shown to be an effective research tool for studying Alzheimer's disease (Morrissette, et al. (2009) *J. Biol. Chem.* 284:6033-6037) was crossed to an ACAT1 (A1−) or ACAT2 (A2−) knock-out mouse (Buhman, et al. (2000) *Biochim. Biophys. Acta* 1529: 142-154) and amyloid pathology development was monitored in the Alzheimer's (Alz) mice with or without ACAT. The results showed that, at 4 month of age, when compared to the control Alz mice, the intraneuronal amyloid-β load in the hypocampal neurons was significantly decreased in the A1−/Alz mice, but not in the A2−/Alz mice. At 17 months of age, when compared to the control Alzheimer's mice, the sizes and densities of the amyloid plaques were significantly decreased in the A1−/Alz mice. Behavioral analysis showed that ACAT1 deficiency rescued the cognitive decline manifested in the Alz mice. These results showed that ACAT1 gene inactivation caused a significant decrease in amyloid pathology in a mouse model for Alzheimer's Disease. Thus, ACAT1, but not ACAT2, is a therapeutic target for treating Alzheimer's Disease.

Example 4

Effect of A1− on Aβ Deposition/hAPPswe Processing, and on hTau

To investigate the effect of inactivating ACAT1 on amyloid and tau pathologies in the 3XTg-Alz mice, A1−/Alz mice were examined used the human specific anti-Aβ antibody 6E10 to perform intraneuronal immunostaining in the CA1 region of hippocampi of 4-month-old mice. Results showed that the staining was significantly diminished (by ~78%) in the A1−/Alz mice. An enzyme-linked immunosorbent assay (ELISA) was next used to measure the total Aβ40 and Aβ42 levels in mouse brain homogenates at 17 months of age. Results showed that the Aβ42 levels were significantly decreased (by ~78%) in A1−/Alz mice; the Aβ40 levels were also decreased, but the difference observed was not statistically significant. Control experiments showed that the brains of nontransgenic mice did not contain measurable Aβ. Thioflavin S was subsequently used to stain amyloid plaques in Alz mouse brains at 17 months of age. The results showed that in A1−/Alz mice the amyloid plaque load in the hippocampi was significantly reduced (by ~77%); in the cortex, the amyloid plaque load in these mice showed a trend toward decreasing (p=0.17).

The effect of A1– on human APP processing in 4-month-old Alz mice was also analyzed. The human-specific anti-Aβ antibody 6E10 was used to detect full-length human APPswe (hAPP), and its proteolytic fragments sAPPα (hsAPPα) (soluble APP fragment produced by α secretase cleavage) and CTFβ (hCTFβ) (C-terminal APP fragment produced by β secretase cleavage) (Thinakaran & Koo (2008) supra). The results showed that in A1–/Alz mice, hsAPPα and hCTFβ levels were decreased (by ~67% and by ~37%, respectively). Unexpectedly, the hAPP level was also significantly reduced (by ~62%). In contrast to the hAPP protein levels, there was no difference in hAPP mRNA levels between the A1+/Alz mice and the A1–/Alz mice. hAPP is synthesized in the endoplasmic reticulum in its immature form (with a molecular weight of ~105-kDa); the immature form moves from the endoplasmic reticulum to the Golgi via the secretory pathway (Cai, et al. (2003) *J. Biol. Chem.* 278:3446-3454), and becomes highly glycosylated (mature form has a molecular weight of ~115-kDa) (Weidemann, et al. (1989) *Cell* 57:115-126; Oltersdorf, et al. (1990) *J. Biol. Chem.* 265:4492-4497; Thinakaran, et al. (1996) *J. Biol. Chem.* 271:9390-9397). Thus, the effects of A1– on the immature and the mature forms of hAPP in young Alz mice (of 25-day old) were examined. The results showed that A1– decreased both forms to approximately the same extent (by ~52-54%), indicating that the effect(s) of A1– occur before newly synthesized hAPP exits the endoplasmic reticulum.

The Alz mice express both hAPP and endogenous (mouse) APP. It is possible that A1– may affect both the hAPP and the mAPP levels. To investigate the total APP levels in Alz mice, a different antibody (antiserum 369) was used, which recognizes the C-terminal fragments of both hAPP and mAPP (Buxbaum, et al. (1990) *Proc. Natl. Acad. Sci. USA* 87:6003-6006). The results showed that there was no detectable difference in the total APP levels between the non-Tg, the A1+/Alz, and the A1–/Alz mice, indicating that in the Alz mice strain, the hAPP is not overexpressed, when compared to the endogenous mAPP protein level. mAPP processing was also examined in mice that did not contain the hAPP gene. In these mice, A1– also did not affect the levels of mAPP (and its homolog APLP2 (Slunt, et al. (1994) *J. Biol. Chem.* 269: 2637-2644)), or any of the proteolytic fragments derived from mAPP. These results led to the conclusion that A1– only reduced the hAPP level, and not the mAPP level. It is known that subtle sequence differences exist between hAPP and mAPP, and these differences may play an important role in causing differential fates of hAPP and mAPP (Du, et al. (2007) *J. Pharmacol. Exp. Ther.* 320:1144-1152; Muhammad, et al. (2008) *Proc. Natl. Acad. Sci. USA* 105:7327-7332). The results herein are in contrast to previous reports that indicated that an ACAT inhibitor affected the proteolytic processing of mouse APP, in addition to affecting the processing of hAPP (Hutter-Paier et al. (2004) supra). The discrepancy between the results herein and those of Hutter-Paier, et al. may be attributable to off-target or side effect(s) of the ACAT inhibitor used in their study.

Tau pathology is one of the hallmarks of Alzheimer's disease. Accordingly, the effect of A1– on mutant human tau (htau) was analyzed in 3XTg-Alz mice. The results showed that at 4 months of age, A1– mice exhibited a significant decrease in htau (by ~57%), but at 17 months of age, A1– mice had an increased level of hyperphosphorylated htau. No significant change was observed in the number of hippocampal neurofibrillary tangles between the A1+/Alz and the A1–/Alz mice. These results indicated that A1– does not attenuate tau pathology in Alz mice.

Example 5

Effect of A1– on Cognitive Deficits of Alz Mice

To determine cognitive deficits of Alz mice, contextual (hippocampus dependent) and cued (amygdala dependent) memory tests were performed on age-matched (2, 9 and 12 months old) A1+/Alz, A1–/Alz and Non-Tg mice. The results showed that mice of all three genotypes at different ages were able to learn equally well. In contextual memory testing, there was no difference among these mice at 2 months of age; at 9 and 12 months, when compared to Non-Tg mice, the A1+/Alz mice exhibited a ~50% deficit, while the A1–/Alz mice exhibited no deficit. In cued memory tests, there was no difference among the mice at 2 months; at 9 months, when compared to Non-Tg mice, the A1+/Alz mice exhibited a trend toward a decline; however, the difference was not statistically significant. At 12 months, a statistically significant memory decline in the A1+/Alz mice was observed. In contrast, the A1–/Alz mice exhibited no deficit at either 9 or 12 months age. These results indicate that A1– ameliorated the hippocampal- and amygdala-dependent cognitive deficits in Alz mice at 9-12 months of age. As a control, contextual and cued tests were also performed on A1+ and A1– mice in the C57BL/6 background at 9 and 12 months of age. The results showed that the A1+ and the A1– mice were able to learn equally well; in either contextual or cued memory tests, wherein the difference between the A1– mice and the A1+ mice was not statistically significant.

Example 6

Effects of A1– on Sterol Metabolism in Alz Mouse Brains

ACAT is an important enzyme in cellular cholesterol homeostasis. It was contemplated that A1– may decrease hAPP content by affecting sterol metabolism in Alz mice brains. To demonstrate this, sterol fractions from A1+/Alz and A1–/Alz mouse brains were isolated and analyzed by GC/MS. The results showed that at 4 months of age, A1 deficiency caused a ~13% decrease in cholesterol content (p=0.04) and a ~32% increase in 24SOH content (p=0.007), without causing significant changes in either lanosterol or desmosterol content. A similar decrease in cholesterol content of the A1–/Alz mouse brains was observed when a colorimetric enzyme assay kit (Wako) as used to determine free cholesterol. It was also found that in the brains of 2-month-old Alz mice, A1 deficiency caused a ~10% decrease in cholesterol content and a ~23% increase in 24SOH content. Subsequently, the relative sterol synthesis and fatty acid synthesis rates were compared in the brains of these mice in vivo. The results showed that A1– caused a ~28% decrease in the sterol synthesis rate (p=0.04) without significantly changing the fatty acid synthesis rate. In mouse brains, cholesteryl ester contents are reported to be very low (Yusuf & Mozaffar (1979) *J. Neurochem.* 32:273-275; Liu, et al. (2009) *Proc. Natl. Acad. Sci. USA* 106:2377-2382). An attempt was made to measure CE in A1+ mice brains by separating the CE fraction from the free cholesterol fraction using column chromatography and determine the cholesterol content in CE by GC/MS after CE was saponified. While the low level of CE prevented a reliable measurement, the results suggested that CE might be present at no more than 1% of the total cholesterol mass in mice brains. Using a similar procedure to determine the 24SOH ester content, it was estimated that no more than 1% of total 24SOH was esterified in the brain. These results are consistent with the finding that ACAT prefers to use cholesterol to various oxysterols as its enzymatic substrate (Zhang, et al. (2003) *J. Biol. Chem.* 278:11642-11647; Liu, et al. (2005) *Biochem. J.* 391:389-397).

To demonstrate the functionality of ACAT1 in the intact mouse brain, a procedure was developed to measure CE synthesis in vivo by injecting $^3$H-labeled cholesterol (as a cyclodextrin complex) into intact mouse brains. The $^3$H-CE produced in A1+ and A1− mice was monitored 3 hours after injection. The result of this experiment showed that in A1+/Alz mice, a small percentage of $^3$H-cholesterol was converted to $^3$H-CE (0.56% in 3 hours); in contrast, such conversion was not detectable in the A1−/Alz mouse brains. This result demonstrated that ACAT1 in intact mouse brains can synthesize CE, although at a low rate.

The data herein indicated that in Alz mouse brains, A1− leads to an increased 24SOH level, which in turn leads to a down-regulation of the sterol synthesis rate. Studies in cell culture have suggested that 24SOH may down-regulate sterol synthesis by two mechanisms, namely by blocking transcriptional activations of SREBP2 target genes, and/or increasing the degradation rate of HMGR protein (Goldstein, et al. (2006) *Cell* 124:35-46). To test the first possibility, the mRNA levels of various SREBP2 and LXR target genes (i.e., HMGR, HMGS, SQS, LRP, LDLR, SREBP2, SREBP1, APOE, ABCA1, ABCG1, ABCG4, and CYP46A1) were compared in the A1+/Alz and the A1−/Alz mouse brains. This analysis indicated no significant alterations in the expression levels of these genes in the brains of mice with or without A1. To test the second possibility, immunoblot analysis was performed on brain homogenates prepared from the Alz mice with or without A1. The result showed that the HMGR protein content was decreased by ~65% in A1−/Alz mouse brains (p=0.0009), while the HMGR mRNA in A1− mice brains was not changed. Additional results showed that in Alz mice at 25-days of age, A1− caused a ~62% decrease in HMGR protein content, demonstrating that the effect of A1− on HMGR content occurs in mice at a young age.

Example 7

Biosynthesis of 24SOH in Hippocampal Neuronal Cell Cultures

The results described herein show that A1−/Alz mouse brains exhibit elevated 24SOH levels, indicating that in mouse neurons, A1− may cause an increase in the biosynthesis of 24SOH. In so far as cultured neurons isolated from brains have been shown to synthesize and secrete 24SOH (Russell, et al. (2009) supra; Kim, et al. (2007) *J. Biol. Chem.* 282:2851-2861), a hippocampal neuronal cell culture system was established from A1+/Alz and A1−/Alz mice to determine whether these cells exhibit an increase in the biosynthesis of 24SOH. CE biosynthesis was monitored in these neurons by incubation with labeled $^3$H-oleic acid. Upon entering cells, $^3$H-oleic acid is rapidly converted to $^3$H-CE by ACAT. Both the A1+ cells and the A1− cells synthesize CE; however, A1− cells synthesize $^3$H-CE at a much reduced capacity compared to A1+ cells. The effect of A1− on 24SOH biosynthesis was subsequently analyzed by feeding neurons with the sterol precursor $^3$H-acetate for 3 hours, then isolating and analyzing the labeled sterols present in the cells and media. The results showed that A1− cells exhibited a reduced trend in cholesterol synthesis rate; the difference observed between A1+ cells and A1− cells approached but did not reach statistical significance (p=0.05). The 24SOH synthesis rate in A1− cells was significantly increased (by ~27%). The $^3$H-sterols in the media of A1+ and A1− cells was also examined. The results showed that the $^3$H-cholesterol contents were not significantly different; in contrast, the $^3$H-24SOH content in A1− cells was significantly (~56%) higher than that in A1+ cells. The percent of total $^3$H-sterols secreted into the media was calculated and it was found that neurons secreted only about 2% of total $^3$H-cholesterol, but secreted 13-15% of total $^3$H-24SOH into the media.

The results herein demonstrate that A1− causes an increased 24SOH biosynthesis rate in neurons. Mouse neurons maintained in culture express CYP46A1 as a single 53-kDa-protein, which can be identified by immunoblot analysis (Russell, et al. (2009) supra). It is possible that the increased synthesis of 24SOH observed in A1− neurons may be due to an increase in CYP46A1 protein content in these neurons. To determine this, CYP46A1 protein content in A1+ and A1− neurons was analyzed by immunoblot analysis. The results showed that the intensities of the 53-kDa-protein band were comparable between the A1+/Alz and A1−/Alz cell types. This result indicates that in hippocampal neurons, the mechanism(s) involved in A1− dependent increase in 24SOH synthesis does not require an increase in CYP46A1 protein content.

Example 8

24SOH Provided to Alz Mouse Neurons Decreases hAPP Protein Content

The observations made in intact A1−/Alz mouse brains (i.e., an increase in 24SOH content and a decrease in hAPP content) indicated that 24SOH may decrease hAPP content in neurons. To test this, hippocampal neurons from A1+/Alz mice were treated with 24SOH, and the hAPP protein content and the HMGR protein content were monitored in parallel. It was found that 1 µM 24SOH rapidly decreased the protein content of both hAPP and HMGR (within 3 hours). A separate experiment showed that 1-5 µM 24SOH caused a rapid decline in hAPP protein content without affecting its mRNA level. This result indicates that accumulation of 24SOH in neurons may down-regulate hAPP protein content in vivo.

Not wishing to be bound by theory, the current findings link cellular cholesterol trafficking with ACAT1, CYP46A1, 24SOH synthesis, and HMGR at the endoplasmic reticulum. In neurons, cholesterol trafficking in and out of the endoplasmic reticulum occurs. The unnecessary buildup of unesterified cholesterol at the endoplasmic reticulum (and other membranes) is toxic (Tabas (2002) *J. Clin. Invest.* 110:905-911; Warner, et al. (1995) *J. Biol. Chem.* 270:5772-5778). To minimize cholesterol accumulation, ACAT1, a resident enzyme located at the endoplasmic reticulum (Chang, et al. (2006) *Annu. Rev. Cell Dev. Biol.* 22:129-157), removes a portion of endoplasmic reticulum cholesterol by converting it to CE. ACAT1 deficiency leads to an increase in the endoplasmic reticulum cholesterol pool and raises the substrate level for CYP46A1, another endoplasmic reticulum resident enzyme (Russell, et al. (2009) supra). This leads to an increase in 24SOH biosynthesis in neurons. The increased 24SOH concentration leads to rapid down-regulation of hAPP protein content, limiting its capacity to produce Aβ. 24SOH secreted by neurons can enter astrocytes and other cell types and lead to efficient down-regulation of HMGR and cholesterol biosynthesis in these cells. Therefore, the beneficial effects of ACAT1 inhibition on cholesterol biosynthesis and on amyloid pathology is attributed to its ability to increase 24SOH level in Alz mouse brains. Therefore, agents that inhibit ACAT1 enzyme activity or decrease ACAT1 gene expression can ameliorate amyloid pathology, and have therapeutic value for treating Alzheimer's disease in humans. These results also indicate that agents that increase the concentration of 24SOH may help to combat Alzheimer's disease by decreasing APP content in the brain. Such agent include, but are not limited to, 24SOH itself.

Example 9

MicroRNA-Mediated Inhibition of ACAT1 Expression

Artificial microRNA molecules were designed to target the 5' end of the coding sequence of mouse ACAT1 sequences listed in Table 2.

TABLE 2

| microRNA | ACAT1 Target Sequence | SEQ ID NO: |
|---|---|---|
| #52 | GGAGCTGAAGCCACTATTTAT | 37 |
| #53 | CTGTTTGAAGTGGACCACATCA | 38 |
| #54 | CCCGGTTCATTCTGATACTGGA | 39 |
| #55 | AACTACCCAAGGACTCCTACTGTA | 40 |

For example, the pre-microRNAs (including sense, antisense and loop regions) of microRNAs #54 and #55 were 5'-TGC TGT CCA GTA TCA GAA TGA ACC GGG TTT TGG CCA CTG ACT GAC CCG GTT CAC TGA TAC TGG A-3' (SEQ ID NO:41) and 5'-TGC TGT ACA GTA GGA GTC CTT GGG TAG TTT TGG CCA CTG ACT GAC TAC CCA AGC TCC TAC TGT A-3' (SEQ ID NO:42), respectively.

NIH-3T3 mouse fibroblasts were transiently transfected with one of several rAAV vectors encoding EmGFP and microRNA (miR) #52, #53, #54 or #55. Forty-eight hours post-transfection, GFP-positive cells were harvested by FACS. GFP-positive cells were washed then lysed in 10% SDS and syringe homogenized. Twenty microgram of protein per sample was subjected to SDS-PAGE. After western blot analysis, bands were quantified with ImageJ. ACAT1 intensity was normalized to GAPDH as a loading control and expressed as relative intensity. The results of this analysis are presented in Table 3.

TABLE 3

| Treatment | Relative Intensity |
|---|---|
| Mock Transfected | 1.00 |
| miR Negative Control | 1.02 |
| miR #52 | 0.77 |
| miR #53 | 0.56 |
| miR #54 | 0.54 |
| miR #55 | 0.39 |

This analysis indicated that microRNA molecules directed to mouse ACAT1 sequences could effectively decrease mouse ACAT1 gene expression by more than 50% compared to untreated controls.

Similarly, upon treatment of human HeLa cells or MCF-7 cells with either of the microRNAs listed in Table 4 (10 nM concentration for two days) decreased human ACAT1 protein expression by 80%.

TABLE 4

| MicroRNA Sequence (5'->3') | SEQ ID NO: |
|---|---|
| CAUGAUCUUCCAGAUUGGAGUUCUA | 43 |
| UAGAACUCCAAUCUGGAAGAUCAUG | 44 |

Example 10

Clinical Assessment of Therapeutic Efficacy

A cohort of subjects fulfilling NINCDS-ADRDA criteria (McKhann, et al. (1984) *Neurology* 34:939-44) for probable or possible AD will be recruited. The median age of the sample group will be determined. Clinical diagnosis will be made independently by, e.g., a psychiatrist and neurologist based on a checklist for symptoms of the disease with strict adherence to NINCDS-ADRDA criteria. Cognitive assessment will be recorded by trained clinical research nurses using the MMSE (Mini Mental State Examination; Folstein et al. (1975) *J. Psychiatric Res.* 12:189-98). Assessment will be followed a standardized protocol to maximize interrater reliability. All subjects will be followed up at yearly intervals, for a period of up to three years or more with repeat MMSE on each occasion.

During the trial period, subjects will either receive regular doses of an ACAT1-selective inhibitor or placebo. The rate of cognitive decline will be based on the average slope of MMSE points change per year. Differences in the average annual MMSE decline in the whole group by the presence or absence of the K variant of the ACAT1-selective inhibitor will be assessed by the Mann-Whitney U test. The subjects will then be grouped into four categories depending on their baseline MMSE scores (e.g., >24; ≦24 and >16; ≦16 and >8; ≦8 points). Differences in the average annual MMSE decline in the four categories by the presence or absence of the K variant of ACAT1-selective inhibitor will be initially assessed by independent t-tests. Linear regression analysis with the average annual MMSE decline as the dependent variable will then be used to assess for confounding and effect modification by the independent variables, e.g., MMSE at baseline, age, age of onset, and sex. It is expected that the results of this analysis will indicate that subjects receiving the ACAT1-selective inhibitor will exhibit a decrease in the rate or severity of cognitive decline as compared to subjects receiving placebo.

Example 11

Specificity of ACAT1 Inhibitors

It has been shown that when the ACAT inhibitor CP113818 or CI 1011 are administered to AD mice, amyloid plaques are significantly reduced and cognitive deficits are rescued, suggesting that inhibiting ACAT may prevent and/or slow down the progression of AD (Hutter-Paier, et al. (2004) supra; Huttunen & Kovacs (2008) supra; Huttunen, et al. (2009) supra). However, close comparison of the instant data and data of the prior art indicates that several important differences exist between the effects of the ACAT inhibitors and the effects of A1. CP113818 inhibits the processing of both human APP and mouse APP, whereas CI 1011 decreases the mature/immature ratio of hAPP. In contrast, A1– only caused a decrease in the full-length human APP protein content and did not affect the mouse APP at any level or alter the mature/immature ratio of hAPP. Another important difference is that unlike the effect of A1−, CP113818 causes a reduction in the full-length hAPP content (Hutter-Paier, et al. (2004) supra). The differences in results indicate that the ACAT inhibitors used in the prior art are not selective for ACAT1.

ACAT is a member of the membrane bound O-acyltransferase (MBOAT) enzyme family (Hofmann (2000) *Trends Biochem. Sci.* 25:111-112), which includes sixteen enzymes with similar substrate specificity and similar catalytic mechanisms, but with diverse biological functions. In addition, many ACAT inhibitors are hydrophobic, membrane active molecules (Homan & Hamelehle (2001) *J. Pharm. Sci.* 90:1859-1867). When administrated to cells, it is likely that they partition into membranes at high concentration, thereby perturbing membrane properties nonspecifically. Although CP113818 and CI 1011 are designated as ACAT inhibitors, they also may inhibit other enzymes in the MBOAT family, and/or interfere with other biological processes.

The present data shows that inactivating the ACAT1 gene alone is sufficient to ameliorate amyloid pathology in the 3XTg-AD mouse model. In this mouse model, A1− acts to reduce Aβ load mainly by reducing the hAPP protein content. In this context, the action of A1− is similar to that of cerebrolysin, a peptide mixture with neurotrophic effects. It has been shown that cerebrolysin reduces Aβ in an AD mouse model, mainly by decreasing the hAPP protein content (Rockenstein, et al. (2006) *J. Neurosci. Res.* 83:1252-1261; Rockenstein, et al. (2007) *Acta Neuropathol.* 113:265-275). To further demonstrate that A1− leads to hAPP content reduction, it was shown that the brains of A1−/Alz mice contain a significantly greater amount of 24SOH. Moreover, in neuron-rich cultures, it was shown that 24SOH, when added to the medium, leads to rapid decrease in hAPP protein content. It is possible that APP may act as a sterol sensing protein (Beel, et al. (2008) *Biochemistry* 47:9428-9446); sequence analysis shows that APP contains three CRAC motifs, a consensus motif known to bind cholesterol (Epand (2008) *Biochim. Biophys. Acta* 1778:1576-1582). It is also possible that cholesterol and/or oxysterol may directly interact with the hAPP protein to accelerate its rate of degradation. Alternatively, 24SOH may act indirectly by reducing membrane cholesterol content.

The data presented herein also show that in mouse brains, A1− caused a decrease in HMGR protein and a decrease in cholesterol biosynthesis. This finding is consistent with previous analysis showing that inhibition of ACAT in macrophages or in CHO cells increases the ER "regulatory sterol pool" that causes down-regulation of HMGR levels and SREBP processing (Tabas, et al. (1986) *J. Biol. Chem.* 261:3147-3155; Scheek, et al. (1997) *Proc. Natl. Acad. Sci. USA* 94:11179-11183). Studies have suggested that the "regulatory sterol" could be cholesterol itself, and/or an oxysterol derived from cholesterol; however, whether oxysterol(s) plays important roles in regulating sterol biosynthesis in the brain in vivo has been debated (Bjorkhem (2009) *J. Lipid Res.* 50:S213-218). To address this issue, it has been shown that knocking out the 24-hydroxylase gene Cyp46a1 causes a near elimination in the 24SOH content, a decrease in cholesterol biosynthesis rate in the brain, and a decrease in cholesterol turnover in the brain; the total brain cholesterol content in the Cyp46a1−/− mice remained unchanged; Cyp46a1−/− did not affect the amyloid pathology in an AD mouse model (Lund, et al. (2003) *J. Biol. Chem.* 278:22980-22988; Kotti, et al. (2006) *Proc. Natl. Acad. Sci. USA* 103:3869-3874; Halford & Russell (2009) *Proc. Natl. Acad. Sci. USA* 106:3502-3506). In contrast, use of a cell-type non-specific promoter to drive the ectopic expression of Cyp46a1 in mouse brains shows that over-expressing Cyp46a1 causes a two-fold increase in 24SOH content and significantly ameliorates amyloid pathology in the AD mice (Hudry, et al. (2010) *Mol. Ther.* 18:44-53). In this study, a reduction in the hAPP protein content was not observed; instead, a decrease in hAPP processing, an increase in SREBP2 mRNA, and no change in brain cholesterol content was demonstrated. The present results show that in the A1−/Alz mice, a 30% increase in 24SOH, a modest reduction in cholesterol biosynthesis rate, in brain cholesterol content, and a significant reduction in amyloid pathology occurred. The Cyp46a1 gene knockout or Cyp46a1 overexpression in mice may have produced compensatory effects that did not occur in the A1− mice, and vice versa; thus a direct comparison of the results described above is difficult. On the other hand, the combined results suggest that 24SOH may play an auxiliary but not an obligatory role in affecting cholesterol metabolism and amyloid biology, and its effects may be cell-type dependent. Based on other evidence, it has been independently proposed that a given oxysterol may play auxiliary but not obligatory roles in regulating cellular cholesterol homeostasis (Brown & Jessup (2009) *Mol. Aspects. Med.* 30:111-122).

The instant data demonstrate a link between ACAT1, CYP46A1, 24SOH synthesis, and HMGR at the ER in cellular cholesterol trafficking. The unnecessary buildup of unesterified cholesterol at the ER (and other membranes) is toxic (Warner, et al. (1995) *J. Biol. Chem.* 270:5772-5778; Tabas (2002) *J. Clin. Invest.* 110:905-911). To minimize cholesterol accumulation, A1, a resident enzyme located at the ER (Sun, et al. (2003) *J. Biol. Chem.* 278:27688-27694), removes a portion of ER cholesterol by converting it to CE. A1− leads to an increase in the ER cholesterol pool and raises the substrate level for CYP46A1, another ER resident enzyme. This leads to an increase in 24SOH biosynthesis in neurons. The increased 24SOH and/or cholesterol concentration in the ER leads to rapid down-regulation of hAPP protein content, perhaps by accelerating its rate of degradation at the ER, thereby limiting its capacity to produce Aβ. 24SOH secreted by neurons can enter astrocytes and other cell types, and lead to efficient down-regulation of HMGR and cholesterol biosynthesis in these cells. Therefore, the beneficial effects of A1− on cholesterol biosynthesis and on amyloid pathology in AD mouse brains is contributed to increase(s) in ER cholesterol and/or 24SOH level in the neurons. Barring the possible side effects caused by altering cholesterol metabolism in the brain, the instant data indicates that agents that selectively and specifically inhibit ACAT1 enzyme activity or decrease ACAT1 gene expression can ameliorate amyloid pathology, and have therapeutic value for treating AD in humans.

What is claimed is:

1. A method for decreasing the size and density of amyloid plaques comprising administering to a subject in need of treatment a microRNA that selectively inhibits the expression of Acyl-CoA:Cholesterol Acyltransferase 1 thereby decreasing the size and density of amyloid plaques in the subject, wherein the microRNA comprises SEQ ID NO. 41, 42, 43 or 44.

2. The method of claim 1, wherein the microRNA is selectively delivered to the brain of the subject.

3. A method for decreasing cognitive decline associated with amyloid pathology comprising administering to a subject in need of treatment a microRNA that selectively inhibits the expression of Acyl-CoA:Cholesterol Acyltransferase 1 thereby decreasing cognitive decline associated with amyloid pathology in the subject, wherein the microRNA comprises SEQ ID NO. 41, 42, 43 or 44.

4. The method of claim 3, wherein the microRNA is selectively delivered to the brain of the subject.

5. A method for treating Alzheimer's Disease comprising administering to a subject in need of treatment a microRNA that selectively inhibits the expression of Acyl-CoA:Cholesterol Acyltransferase 1 thereby treating the subject's Alzheimer's Disease, wherein the microRNA comprises SEQ ID NO. 41, 42, 43 or 44.

6. The method of claim 5, wherein the microRNA is selectively delivered to the brain of the subject.

* * * * *

UNITED STATES PATENT AND TRADEMARK OFFICE
CERTIFICATE OF CORRECTION

PATENT NO. : 8,466,121 B2
APPLICATION NO. : 13/072915
DATED : June 18, 2013
INVENTOR(S) : Chang and Chang It is certified that error appears in the above-identified patent and that said Letters Patent is hereby corrected as shown below:

In the Specification:

In column 19, line 1, please delete "A1-,CP113818"

In column 19, line 1, please insert -- CP113818, A1- -- after "of"

Signed and Sealed this
Fifteenth Day of October, 2013

Teresa Stanek Rea
*Deputy Director of the United States Patent and Trademark Office*

SEQUENCE LISTING

<160> NUMBER OF SEQ ID NOS: 44

<210> SEQ ID NO 1
<211> LENGTH: 30

```
<212> TYPE: DNA
<213> ORGANISM: Artificial Sequence
<220> FEATURE:
<223> OTHER INFORMATION: Synthetic oligonucleotide

<400> SEQUENCE: 1
agcccagaaa aatttcatgg acacatacag                                          30

<210> SEQ ID NO 2
<211> LENGTH: 30
<212> TYPE: DNA
<213> ORGANISM: Artificial Sequence
<220> FEATURE:
<223> OTHER INFORMATION: Synthetic oligonucleotide

<400> SEQUENCE: 2
cccttgttct ggaggtgctc tcagatcttt                                          30

<210> SEQ ID NO 3
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 3
tttgctctat gcctgcttca                                                     20

<210> SEQ ID NO 4
<211> LENGTH: 21
<212> TYPE: DNA
<213> ORGANISM: Artificial Sequence
<220> FEATURE:
<223> OTHER INFORMATION: Synthetic oligonucleotide

<400> SEQUENCE: 4
ccatgaagag aaaggtccac a                                                   21

<210> SEQ ID NO 5
<211> LENGTH: 18
<212> TYPE: DNA
<213> ORGANISM: Artificial Sequence
<220> FEATURE:
<223> OTHER INFORMATION: Synthetic oligonucleotide

<400> SEQUENCE: 5
atggtgaagg tcggtgtg                                                       18

<210> SEQ ID NO 6
<211> LENGTH: 18
<212> TYPE: DNA
<213> ORGANISM: Artificial Sequence
<220> FEATURE:
<223> OTHER INFORMATION: Synthetic oligonucleotide

<400> SEQUENCE: 6
cattctcggc cttgactg                                                       18

<210> SEQ ID NO 7
<211> LENGTH: 18
<212> TYPE: DNA
<213> ORGANISM: Artificial Sequence
<220> FEATURE:
<223> OTHER INFORMATION: Synthetic oligonucleotide

<400> SEQUENCE: 7
acggcgctga aggagatc                                                       18
```

<210> SEQ ID NO 8
<211> LENGTH: 18
<212> TYPE: DNA
<213> ORGANISM: Artificial Sequence
<220> FEATURE:
<223> OTHER INFORMATION: Synthetic oligonucleotide

<400> SEQUENCE: 8
gtccagggcc atcttgac                                              18

<210> SEQ ID NO 9
<211> LENGTH: 21
<212> TYPE: DNA
<213> ORGANISM: Artificial Sequence
<220> FEATURE:
<223> OTHER INFORMATION: Synthetic oligonucleotide

<400> SEQUENCE: 9
cccactgatg gtaatgctgg c                                          21

<210> SEQ ID NO 10
<211> LENGTH: 21
<212> TYPE: DNA
<213> ORGANISM: Artificial Sequence
<220> FEATURE:
<223> OTHER INFORMATION: Synthetic oligonucleotide

<400> SEQUENCE: 10
ggaatcacaa agtggggatg g                                          21

<210> SEQ ID NO 11
<211> LENGTH: 28
<212> TYPE: DNA
<213> ORGANISM: Artificial Sequence
<220> FEATURE:
<223> OTHER INFORMATION: Synthetic oligonucleotide

<400> SEQUENCE: 11
ggtttggaga tggttataca atagttgt                                   28

<210> SEQ ID NO 12
<211> LENGTH: 18
<212> TYPE: DNA
<213> ORGANISM: Artificial Sequence
<220> FEATURE:
<223> OTHER INFORMATION: Synthetic oligonucleotide

<400> SEQUENCE: 12
ttcccggaaa cgcaagtc                                              18

<210> SEQ ID NO 13
<211> LENGTH: 25
<212> TYPE: DNA
<213> ORGANISM: Artificial Sequence
<220> FEATURE:
<223> OTHER INFORMATION: Synthetic oligonucleotide

<400> SEQUENCE: 13
aggtctcagc cttctaaagt tcctc                                      25

<210> SEQ ID NO 14
<211> LENGTH: 26
<212> TYPE: DNA
<213> ORGANISM: Artificial Sequence
<220> FEATURE:
<223> OTHER INFORMATION: Synthetic oligonucleotide

```
<400> SEQUENCE: 14
tctctcgaag tgaatgaaat ttatcg                                            26

<210> SEQ ID NO 15
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 15
ctgtcctatt ccgtgcggga                                                   20

<210> SEQ ID NO 16
<211> LENGTH: 24
<212> TYPE: DNA
<213> ORGANISM: Artificial Sequence
<220> FEATURE:
<223> OTHER INFORMATION: Synthetic oligonucleotide

<400> SEQUENCE: 16
gggacttcat gagggacacc actt                                              24

<210> SEQ ID NO 17
<211> LENGTH: 22
<212> TYPE: DNA
<213> ORGANISM: Artificial Sequence
<220> FEATURE:
<223> OTHER INFORMATION: Synthetic oligonucleotide

<400> SEQUENCE: 17
agccaatagt ggaagacatg ca                                                22

<210> SEQ ID NO 18
<211> LENGTH: 24
<212> TYPE: DNA
<213> ORGANISM: Artificial Sequence
<220> FEATURE:
<223> OTHER INFORMATION: Synthetic oligonucleotide

<400> SEQUENCE: 18
gcaggacagg agaaggatac tcat                                              24

<210> SEQ ID NO 19
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 19
cagtgaaggt catgctggag                                                   20

<210> SEQ ID NO 20
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 20
cgcaatgaag aaggtgacaa                                                   20

<210> SEQ ID NO 21
<211> LENGTH: 23
```

```
<212> TYPE: DNA
<213> ORGANISM: Artificial Sequence
<220> FEATURE:
<223> OTHER INFORMATION: Synthetic oligonucleotide

<400> SEQUENCE: 21
tctggcagtc agtgggaact att                                              23

<210> SEQ ID NO 22
<211> LENGTH: 21
<212> TYPE: DNA
<213> ORGANISM: Artificial Sequence
<220> FEATURE:
<223> OTHER INFORMATION: Synthetic oligonucleotide

<400> SEQUENCE: 22
cctcgtcctt cgatccaatt t                                                21

<210> SEQ ID NO 23
<211> LENGTH: 18
<212> TYPE: DNA
<213> ORGANISM: Artificial Sequence
<220> FEATURE:
<223> OTHER INFORMATION: Synthetic oligonucleotide

<400> SEQUENCE: 23
gccgtcaact gggtcgaa                                                    18

<210> SEQ ID NO 24
<211> LENGTH: 24
<212> TYPE: DNA
<213> ORGANISM: Artificial Sequence
<220> FEATURE:
<223> OTHER INFORMATION: Synthetic oligonucleotide

<400> SEQUENCE: 24
gcatatatag caatgtctcc tgca                                             24

<210> SEQ ID NO 25
<211> LENGTH: 22
<212> TYPE: DNA
<213> ORGANISM: Artificial Sequence
<220> FEATURE:
<223> OTHER INFORMATION: Synthetic oligonucleotide

<400> SEQUENCE: 25
ttgctcgaga tgtcatgaag ga                                               22

<210> SEQ ID NO 26
<211> LENGTH: 25
<212> TYPE: DNA
<213> ORGANISM: Artificial Sequence
<220> FEATURE:
<223> OTHER INFORMATION: Synthetic oligonucleotide

<400> SEQUENCE: 26
agcaggtcag caaagaactt atagc                                            25

<210> SEQ ID NO 27
<211> LENGTH: 22
<212> TYPE: DNA
<213> ORGANISM: Artificial Sequence
<220> FEATURE:
<223> OTHER INFORMATION: Synthetic oligonucleotide

<400> SEQUENCE: 27
ctgtgggctc cataggctat ct                                               22
```

<210> SEQ ID NO 28
<211> LENGTH: 19
<212> TYPE: DNA
<213> ORGANISM: Artificial Sequence
<220> FEATURE:
<223> OTHER INFORMATION: Synthetic oligonucleotide

<400> SEQUENCE: 28
gcggtccagg gtcatcttc					19

<210> SEQ ID NO 29
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 29
tgggtctccc gaaatctgtt					20

<210> SEQ ID NO 30
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 30
accaccgcat tcttgaagga					20

<210> SEQ ID NO 31
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 31
aaccagaagc tcaagcagga					20

<210> SEQ ID NO 32
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 32
tcatgccctc catagacaca					20

<210> SEQ ID NO 33
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 33
gtggagcagt ctcaacgtca					20

<210> SEQ ID NO 34
<211> LENGTH: 20
<212> TYPE: DNA
<213> ORGANISM: Artificial Sequence
<220> FEATURE:
<223> OTHER INFORMATION: Synthetic oligonucleotide -continued

<400> SEQUENCE: 34
tggtaggtct cacccaggag                                                20

<210> SEQ ID NO 35
<211> LENGTH: 22
<212> TYPE: DNA
<213> ORGANISM: Artificial Sequence
<220> FEATURE:
<223> OTHER INFORMATION: Synthetic oligonucleotide

<400> SEQUENCE: 35
ccaactcaat gggtctgttc ct                                             22

<210> SEQ ID NO 36
<211> LENGTH: 23
<212> TYPE: DNA
<213> ORGANISM: Artificial Sequence
<220> FEATURE:
<223> OTHER INFORMATION: Synthetic oligonucleotide

<400> SEQUENCE: 36
tggcttagca aagtcttcca act                                            23

<210> SEQ ID NO 37
<211> LENGTH: 21
<212> TYPE: DNA
<213> ORGANISM: Artificial Sequence
<220> FEATURE:
<223> OTHER INFORMATION: Synthetic oligonucleotide

<400> SEQUENCE: 37
ggagctgaag ccactattta t                                              21

<210> SEQ ID NO 38
<211> LENGTH: 22
<212> TYPE: DNA
<213> ORGANISM: Artificial Sequence
<220> FEATURE:
<223> OTHER INFORMATION: Synthetic oligonucleotide

<400> SEQUENCE: 38
ctgtttgaag tggaccacat ca                                             22

<210> SEQ ID NO 39
<211> LENGTH: 22
<212> TYPE: DNA
<213> ORGANISM: Artificial Sequence
<220> FEATURE:
<223> OTHER INFORMATION: Synthetic oligonucleotide

<400> SEQUENCE: 39
cccggttcat tctgatactg ga                                             22

<210> SEQ ID NO 40
<211> LENGTH: 24
<212> TYPE: DNA
<213> ORGANISM: Artificial Sequence
<220> FEATURE:
<223> OTHER INFORMATION: Synthetic oligonucleotide

<400> SEQUENCE: 40
aactacccaa ggactcctac tgta                                           24

<210> SEQ ID NO 41
<211> LENGTH: 64

```
<212> TYPE: DNA
<213> ORGANISM: Artificial Sequence
<220> FEATURE:
<223> OTHER INFORMATION: Synthetic oligonucleotide

<400> SEQUENCE: 41
tgctgtccag tatcagaatg aaccgggttt tggccactga ctgacccggt tcactgatac      60
tgga                                                                  64

<210> SEQ ID NO 42
<211> LENGTH: 64
<212> TYPE: DNA
<213> ORGANISM: Artificial Sequence
<220> FEATURE:
<223> OTHER INFORMATION: Synthetic oligonucleotide

<400> SEQUENCE: 42
tgctgtacag taggagtcct tgggtagttt tggccactga ctgactaccc aagctcctac      60
tgta                                                                  64

<210> SEQ ID NO 43
<211> LENGTH: 25
<212> TYPE: RNA
<213> ORGANISM: Artificial sequence
<220> FEATURE:
<223> OTHER INFORMATION: Synthetic oligonucleotide

<400> SEQUENCE: 43
caugaucuuc cagauuggag uucua                                            25

<210> SEQ ID NO 44
<211> LENGTH: 25
<212> TYPE: RNA
<213> ORGANISM: Artificial sequence
<220> FEATURE:
<223> OTHER INFORMATION: Synthetic oligonucleotide

<400> SEQUENCE: 44
uagaacucca aucuggaaga ucaug                                            25
```